United States Patent
Xu et al.

(10) Patent No.: US 10,568,843 B2
(45) Date of Patent: Feb. 25, 2020

(54) METHOD OF PREPARING HIGHLY STABLE MICROCAPSULE POWDERS OR MICROPARTICLES CONTAINING FAT-SOLUBLE NUTRIENT HAVING INCREASED DOUBLE BONDS

(71) Applicant: Zhejiang Medicine Co., Ltd. Xinchang Pharmaceutical Factory, Xinchang County (CN)

(72) Inventors: Xinde Xu, Xinchang County (CN); Di Zhou, Xinchang County (CN); Lihua Zhang, Xinchang County (CN); Bin Shao, Xinchang County (CN)

(73) Assignee: Zhejiang Medicine Co., Ltd, Zhejiang (CN)

( * ) Notice: Subject to any disclaimer, the term of this patent is extended or adjusted under 35 U.S.C. 154(b) by 0 days.

(21) Appl. No.: 15/767,772

(22) PCT Filed: Oct. 12, 2015

(86) PCT No.: PCT/CN2015/000688
§ 371 (c)(1),
(2) Date: Apr. 12, 2018

(87) PCT Pub. No.: WO2017/063101
PCT Pub. Date: Apr. 20, 2017

(65) Prior Publication Data
US 2018/0303761 A1 Oct. 25, 2018

(51) Int. Cl.
*A61K 9/50* (2006.01)
*A61K 47/36* (2006.01)
*A61K 47/42* (2017.01)
*A61K 47/22* (2006.01)

(52) U.S. Cl.
CPC .......... *A61K 9/5089* (2013.01); *A61K 9/5036* (2013.01); *A61K 9/5057* (2013.01); *A61K 47/36* (2013.01); *A61K 47/42* (2013.01); *A61K 47/22* (2013.01)

(58) Field of Classification Search
None
See application file for complete search history.

(56) References Cited

U.S. PATENT DOCUMENTS

2005/0226858 A1 * 10/2005 Kitamura ............. A61K 31/015
424/94.1

FOREIGN PATENT DOCUMENTS

CN 1969833 A * 5/2007
CN 101559045 A * 10/2009

OTHER PUBLICATIONS

English Translation of CN1969833A. Obtained from Google Patents at https://patents.google.com/patent/CN1969833A/en?oq=CN+1969833 on Nov. 6, 2018. Originally published in Chinese on May 30, 2007, pp. 1-5 (Year: 2007).*
English Translation of CN101559045A. Obtained from Google Patents at https://patents.google.com/patent/CN101559045A/en?oq=CN+101559045 on Nov. 7, 2018, originally published in Chinese on Oct. 21, 2009, pp. 1-5. (Year: 2009).*
ZH Lo, DZL Er, LW Chan, CV Liew, PWS Heng. "Spray granulation for drug formulation." Expert Opinion in Drug Delivery, vol. 8(12), 2011, pp. 1645-1661. (Year: 2011).*

* cited by examiner

Primary Examiner — Isaac Shomer
(74) Attorney, Agent, or Firm — Christopher Casieri

(57) ABSTRACT

The present invention provides a method of preparing highly stable microcapsule powders or microparticles containing a fat-soluble nutrient having multiple double bonds. The method includes a) dissolving the fat-soluble nutrient having multiple unsaturated double bonds to prepare an oil phase; b) dissolving a part of a capsule shell material into water to prepare an aqueous phase; c) shearing the aqueous phase and the oil phase, and mixing and emulsifying the same to obtain an emulsion; d) homogenizing the emulsion by a standard high-pressure homogenizer, to make the emulsion obtain droplets in the emulsion with an average particle diameter at a nanometer level, thereby producing a nanometer scale emulsion; e) directly adding a remaining part of the capsule shell material into the homogenized nanometer scale emulsion, and shearing, mixing, and dissolving the same to obtain a twice-embedded emulsion; and f) performing spray granulation on the twice-embedded emulsion, and drying resultant granules to obtain the highly stable microcapsule powder or microparticles.

8 Claims, No Drawings

METHOD OF PREPARING HIGHLY STABLE MICROCAPSULE POWDERS OR MICROPARTICLES CONTAINING FAT-SOLUBLE NUTRIENT HAVING INCREASED DOUBLE BONDS

FIELD OF THE INVENTION

The present invention relates to a method of preparing highly stable microcapsule powders or microparticles containing a fat-soluble nutrient having multiple double bonds. In particular, the present invention consciously changes the emulsion viscosity before high pressure homogenization by creatively changing an adding order of capsule shell materials, in order to obtain a smaller particle diameter droplet in the emulsion under lower pressure and make microcapsule powders or microparticles quite stable without an objectionable odor.

BACKGROUND OF THE INVENTION

As people pay attention to their health, more and more people would like to daily take some vitamins and healthy dietary components to keep their health. These vitamins and healthy dietary components include fat-soluble nutrients such as VA, VE, and VD3; polyunsaturated fatty acids such as ω-3, ω-6, and ω-9; carotenoids such as beta-carotene, lutein, zeaxanthin, astaxanthin, ycopene, and curcumin; as well as retinoids such as coenzymes Q10.

Because of multiple double bonds in the molecular structures of these nutrients, these nutrients have health functions. These double bonds can highly eliminate free radicals in the human body and have antioxidant ability. Free radicals are one of the most important reasons of producing aging and other diseases. It has been estimated that 80%-90% of aging and degenerative diseases are associated with free radicals, wherein these diseases include cancer, Alzheimer's disease, Parkinson's disease, skin spots deposition, cataract, heart disease and so on. So it is of great importance for keeping one's body healthy and young to eliminate harmful free radicals.

These nutrients have the following structure and efficacy:

Vitamin A

Vitamin A is a very important member in the fat-soluble nutrients family and has a very important function on visual health, bone health, reproduction and cell division and reproduction. It would be inconceivable for the lack of vitamin A in the human body. Vitamin A mainly exists in the form of vitamin A alcohol (structure provided below), vitamin A acetate and vitamin A palmitate.

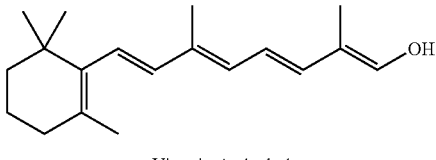

Vitamin A alcohol

Vitamin E

Vitamin E is an important anti-oxidation agent derived from nature and synthesis. Vitamin E exists in eight forms of monomers such as alpha-vitamin E, beta-vitamin E, gamma-vitamin E, and delta-vitamin E, each of the monomers has two different optical isomers. Alpha-Vitamins E including such as free type tocopherol, tocopherol acetate, tocopherol succinate and tocopheryl nicotinate are widely used in the market.

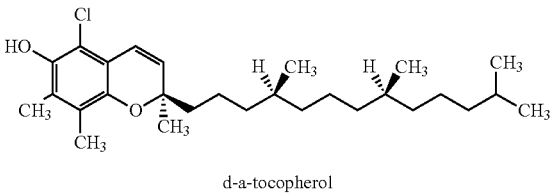 [SMILES: Cc1c(C)c2c(c(Cl)c1O)C=C[C@@](C)(CCC[C@@H](C)CCC[C@@H](C)CCCC(C)C)O2]

d-a-tocopherol

Polyunsaturated Fatty Acids (PUFA)

Polyunsaturated fatty acids are essential for the human body and mainly play a role on physiological functions such as maintaining cell membrane fluidity to assure normal physiological function of cells, promoting cholesterol esterfication, reducing cholesterol and triglycerides levels of blood, decreasing blood viscosity, and improving blood circulation, increasing activity of brain cells and enhancing memory and improving human thinking.

Polyunsaturated fatty acids mainly comprises ω-3 PUFA such as α-linolenic acid, Eicosapentaenoic acid, Docosahexaenoic acid and docosapentaenoic acid and ω-6 PUFA such as Linoleic acid, Conjugated Linoleic acid, γ-Linolenic, Arachidonic Acid. The molecular structures of these polyunsaturated fatty acids are as follows:

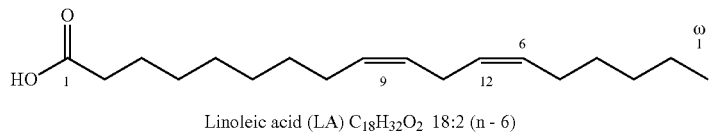

Linoleic acid (LA) $C_{18}H_{32}O_2$ 18:2 (n - 6)

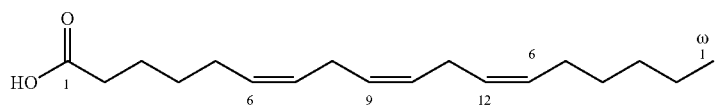

Gamma-Linolenic acid (GLA) $C_{18}H_{30}O_2$ 18:3 (n - 6)

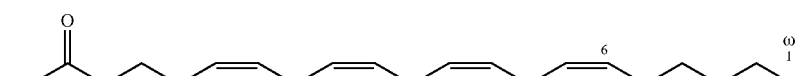

Arachidonic acid (AA) $C_{20}H_{32}O_2$ 20:4 (ω-6)

-continued

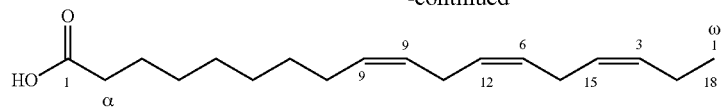

Alpha-linolenic acid (ALA) $C_{18}C_{30}O_2$ 18:3 (n-3)

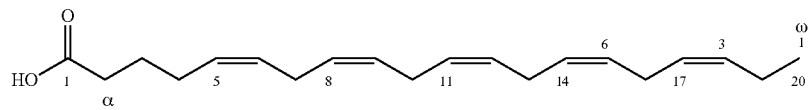

Eicosapentaenoic acid (EPA) $C_{20}H_{30}O_2$ 20:5 (n-3)

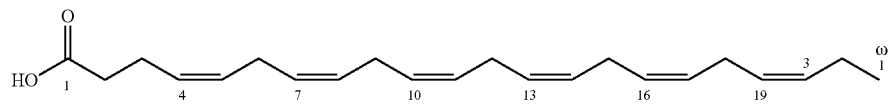

Docosahexaenoic acid (DHA) $C_{22}H_{32}O_2$ 22:6 (ω-3)

The fish oils derived from abyssopelagic fishes such as anchovy, tuna and squid mainly comprise polyunsaturated fatty acids EPA and DHA. DHA and EPA are also derived from cultured algae.

Carotenoids

Carotenoids are synthesised by plants and exist in nature in the form of pigments. There are more than 600 kinds of known carotenoids, wherein beta-carotenoids, lycopene, astaxanthin, lutein and cryptoxanthin are more important carotenoids. Some carotenoids can be converted to Vitamin A having physiological effects on the human body and the animal body and thus are known as "provitamin A".

Carotenoids have main functions as follows: the most effective antioxidants against free radicals; enhancing immune system, increasing resistibility; preventing or fighting against cancer; decreasing risks of oral cancer, breast cancer, cervical cancer, lung cancer, trachea cancer, esophagus cancer, stomach cancer, bladder cancer; preventing heart and vascular diseases; preventing cataract, protecting fiber parts of eyes crystal; improving urinary system, preventing prostate problem; improving tendonitis and adhesive capsulitis caused by rheumatic arthritis tendinitis, being natural eye drops, maintaining lubrication and transparency of cornea and promoting health of eyes; being the precursor of VA, keeping healthy of skin and organ cavity mucosa.

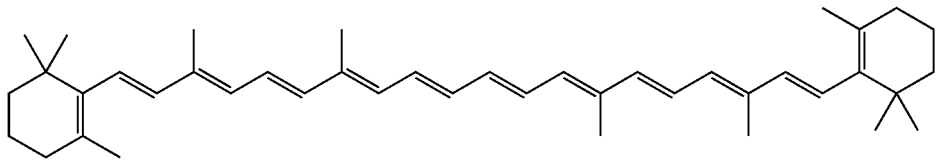

β-carotene ($C_{40}H_{56}$, M = 536.88)

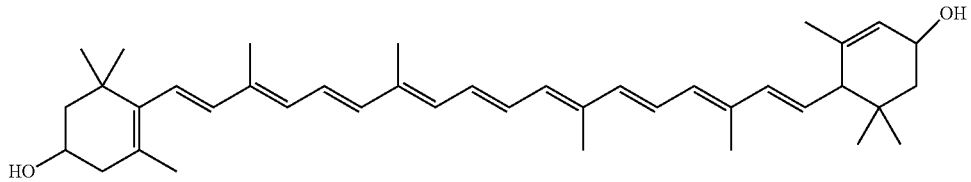

lutein ($C_{40}H_{56}O_2$, M = 568.88)

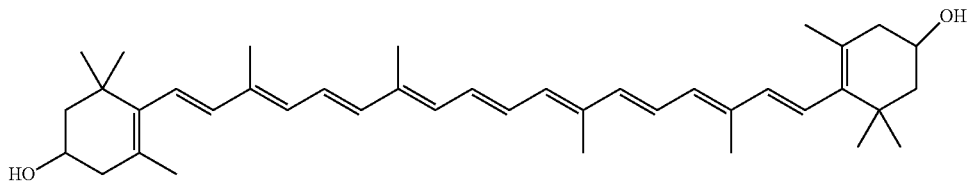

zeaxanthin ($C_{40}H_{56}O_2$, M = 568.88)

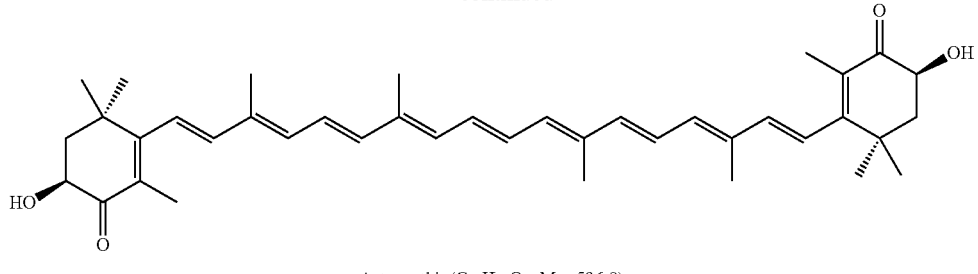

Astaxanthin($C_{40}H_{52}O_4$, M = 596.8)

Curcumin

Curcumin is a very prospective nutrient and has functions such as resisting oxidation, scavenging free radicals, anti-inflammatory, anti-freezing, regulating blood lipid, anti-lipid peroxidation, inhibiting formation of plaque, inhibiting proliferation of vascular smooth muscle cells. Its molecular structures is as follows:

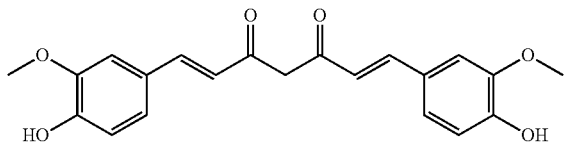

Curcumin ($C_{21}H_{20}O_6$, M = 368.4)

Coenzymes Q10

Coenzyme Q10 is a fat-soluble compound widely existing in organisms and widely distributed in nature, mainly in yeast, plant leaves, seeds and cells of heart, liver and kidney of animals. Coenzyme Q10 is one of the most important coenzymes in the human body. The main function of coenzyme Q10 is to scavenge free radicals, anti-tumor activity, enhance immunity, promote metabolism and improve hypoxia tolerance of the heart, etc.

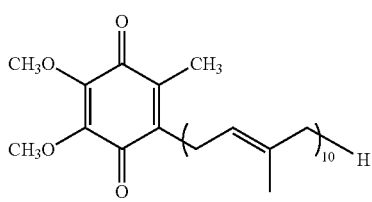

Coenzymes Q10 ($C_{21}H_{20}O_6$, M = 368.4)

It may be seen that the above nutrients have at least two common features: 1) having fat-soluble characteristics, and 2) having multiple double bonds in the molecular structure.

It would highly limit their application scopes and application modes due to fat-soluble characteristics. So their nutrients are used in the oil-based food or administered in the form of soft capsules or modified to become water soluble and thus used in the water-based foods. An important method of changing its solubility is to change fat-soluble nutrients into water soluble nutrients by microcapsules.

On the one hand, multiple double bonds provide the nutrients for antioxygenic property and scavenging free radicals and reflecting its physiological function. On the other hand, multiple double bonds make the nutrients very unstable in the storage process or in the process of microcapsule processing because of heat and light and consequently cause the nutrients to have reduced biological activity, especially it makes a degradation process more obvious in higher pressure and heating.

Many methods for preparing fat soluble nutrient microcapsules have been reported in the prior art.

US Patent No. 2007/0128341 discloses a method of preparing polyunsaturated fatty acids by lactoprotein, in particular a method of preparing a polyunsaturated fatty acid microcapsule emulsion or powders from fish oils by using lactoprotein and polyunsaturated fatty acids, to obtain a microcapsule.

US Patent No. 2008/0254184 describes a formulation and method of preparing polyunsaturated fatty acids microcapsule using Arabic gum. But the method only uses Arabic gum in the capsule shell materials. It certainly limits its application.

Chinese Patent No. 101177540B discloses a method of preparing water-soluble carotenoids microcapsule powder. In particular, carotenoids dissolved in organic solvents are mixed with water and homogenized under high pressure, high temperature and high viscosity to obtain an emulsion. A great amount of water is added for reducing the viscosity of the emulsion due to high pressure in the process. It certainly produces waste of energy and operation because of removing the water before spraying and prilling.

Chinese Patent No. 1022278257A relates to a method of preparing an algal oil DHA (Docosahexaenoic Acid) microcapsule. In particular, modified starch and Arabic gum as capsule shell materials are added in separate steps, and then an emulsifier, an aqueous phase, an emulsion phase and a combined phase, emulsion are respectively prepared. The process goes through several mixing, shearing, and homogenization. And a greater amount of water is added to achieve homogenization effects. Especially the requires removing water before spraying and drying. So the process is long and complex, with a low degree of efficiency.

In general, some products made by the methods of preparing fat-soluble nutrients microcapsule containing multiple double bonds in the art have poor stability, fall short of expectation, complex process, lower efficiency; and severe conditions. It would be very difficult to achieve in the industry. So it is necessary to find a simple method for preparing a highly stable, water soluble microcapsule.

The inventors of the present invention found that the stability of fat-soluble nutrients microcapsule containing multiple double bonds has something to do with not only the formulation but also the processing technology of the process. For example, the stability of the final microcapsule product is closely related to emulsion degrees of aqueous phase and oil phase, and sizes of oil-in-water emulsion. The more uniform a mixture of oil phase and aqueous phase is, the smaller particle diameter of oil droplet oil in water emulsion droplet is, the more stable is the final microcapsule product. That is why the oil phase and the aqueous phase are completely mixed during the preparation process of microcapsule and the obtained emulsion needs conducting high pressure homogenization.

After shearing and emulsifying, the particle diameter of the emulsion droplet is micron-sized. the emulsion containing bigger particle diameter droplet is homogenized under a high pressure (generally more than 10 Mpa) to improve the stability of final product. After homogenization, the micron-sized droplets are smashed smaller up to nanoscale droplets. These nanoscale droplets are to the benefit of not only increasing the bioavailability of final product, but also being completely embedded, in order to prevent from aggregation of larger-sized particles and improve the stability of final product.

During the process of homogenizing micron-sized droplets emulsion under high pressures, the homogenization effect of the emulsion is closely related to the viscosity of the emulsion. The smaller the viscosity is, the lower the homogenization pressure is, the better the homogenization effect is. It means that the smaller the particle diameter of oil in water emulsion droplet is, the more stability the final microcapsule product has. Besides, the emulsion can obtain more energy in high pressures of homogenization due to high pressure functions, so as to make emulsion temperature increased more easily, even up to more than 20° C. The higher the pressure is, the more the emulsion temperature rises. But increasing the emulsion temperature is very unfavorable for the stability of nutrients containing multiple double bonds. On the one hand, increasing temperature may easily degrade these unstable nutrients, and even may produce some new unexpected degradation products. On the other hand, existing in a high temperature for a long time will make the microcapsule product unstable. It means that the stability of lots of fat-soluble nutrients microcapsule products containing multiple double bonds, especially polyunsaturated fatty acid microcapsule powders from fish oils, is not good. The content of effective components will decrease over time. This is why the product produces an obvious fishy odor after storage for quite a while. These problems cannot be effectively solved, even though taking various measures such as adding numbers of antioxidants, double encapsulating, and increasing proportion of capsule shell materials.

SUMMARY OF THE INVENTION

In order to solve the above problems, the present invention creatively provides a method of first dissolving a part of a capsule shell material into water to obtain an aqueous phase, and mixing with an oil phase and shearing and emulsifying to form an emulsion, and then homogenizing the emulsion at low pressure, adding a remaining portion of the capsule shell material into the emulsion; directly spraying granulation the emulsion after completely dissolved to obtain a microcapsule product. The microcapsule product is quite stable without objectionable odor after storage for a long time. More importantly, the microcapsule product has good resistance to pressure. The microcapsule product still has a better stability after tabletting. In order to overcome these disadvantages in the art, the present invention provide a method of preparing highly stable microcapsule powders or microparticles containing a fat-soluble nutrient having multiple double bonds.

In particular, the method comprises the following steps: a) dissolving a fat-soluble nutrient having multiple unsaturated double bonds to prepare an oil phase; b) dissolving a part of a capsule shell material into water to prepare an aqueous phase; c) shearing the aqueous phase and the oil phase, and mixing and emulsifying the same to obtain an emulsion; d) homogenizing the emulsion by a standard high-pressure homogenizer, to make the emulsion obtain droplets in the emulsion with an average particle diameter at a nanometer level, thereby producing a nanometer scale emulsion; e) directly adding a remaining part of the capsule shell material into the homogenized nanometer scale emulsion, and shearing, mixing and dissolving the same to obtain a twice-embedded emulsion; and f) performing spray granulation on the twice-embedded emulsion, and drying resultant granules to obtain highly stable microcapsule powders or microparticles.

The "Fat-soluble nutrient having multiple unsaturated double bonds" of the present invention is referred to as a substance having double bonds in its molecular structure, being fat-soluble and in favor of human health. The fat-soluble nutrient having multiple unsaturated double bonds is selected from the group consisting of VA, VE, natural VE, VD3, coenzymes Q10, curcumin, carotenoid and polyunsaturated fatty acid. The carotenoid is beta-carotene, lutein, astaxanthin, ycopene, and zeaxanthin; the polyunsaturated fatty acid is derived from animal extract oil, fermented source and synthetic source; the polyunsaturated fatty acid comprises conjugated linoleic acid, arachidonic acid, linoleic acid, linolenic acid, EPA, DHA and mixtures thereof. These nutrients are unstable to heat, oxygen and light and are easily influenced by processing conditions due to these nutrients having multiple double bonds. It would produce certain degradation products, polymers or isomerization. These not only would decrease the health effects of the microcapsule products, but also would produce some unpleasant odor and affect its usage.

The "capsule shell material" of the present invention is referred to as the nutrient being embedded to form a microcapsule in order to separate the nutrition from air. The capsule shell material comprises is but not limited to an animal capsule shell material such as gelatin, and a vegetable capsule shell material such as Arabic gum, modified starch and sodium caseinate. Preferably, the vegetable capsule shell material is Arabic gum and modified starch with the strength of sensibility for animal source materials.

The "nanoscale" of the present invention is referred to as that when, an average particle diameter of the droplet is less than 1 μm after the microcapsule emulsion, microcapsule powder or microparticle is dispersed in water.

The "high stability" of the present invention is referred to as the microcapsule powder or microparticle having stability, and especially having better stability after tabletting. Such high stability can be measured by analytical testing and reliance on test results The microcapsule powders or microparticles are sealed and packaged and then stored at 40° C. It may be shown from the result of determination that the retention rate of the content is still more than 90% after 3 months, by respectively determining their content after 0, 1, 2 or 3 months.

The microcapsule powders or microparticles are directly tabletted without any excipients, and sealed, packaged and then stored at 40° C. It may be shown from the result of determination that the retention rate of the content is still more than 85% after 3 months, by respectively determining their content after 0, 1, 2 or 3 months.

Determining a quantitatively unpleasant odor of the microcapsule powders or nricroparticles may be undertaken by a common electronic nose besides smelling.

Determination method: determining a broad spectrum handheld volatile organic compounds (VOC) gas detector. Type: MiniRAE 3000.

Determination step: To add 10 g sample into a jar and close a cap of the jar, and place the jar into a water bath at 60° C. for 10 minutes; afterwards open the cap, place a probe of the detector on the bottle mouth of the jar, and record information on the odor associated with the sample.

If necessary, water soluble antioxidants such as vitamin C and ascorbic acid may be added to the aqueous phase of the present invention. Fat-soluble antioxidants such as tocopherol, mixed tocopherol, ascorbyl palmitate, lecithin, and rosemary may be added to the oil phase. These antioxidants are beneficial to the stability of nutrients in the final microcapsule powders or microparticles products.

High pressure homogenization is a common method to make the droplet particle diameter smaller, and a smaller particle diameter droplet in the emulsion is very important for the absorption and stability of the emulsion or microcapsule powders or microparticles in the human body. A smaller particle diameter droplet is beneficial to the absorption of nutrients in the human body, and is also beneficial to the stability of the products. As is well known, an emulsion or microcapsule powder or microparticle is a heterogeneous system. As for a fat-soluble oil phase dispersed in a continuous phase of capsule shell materials, it would require particle diameter of the nutrients droplet in a dispersed state as small as possible and uniformly dispersed in a continuous phase in order to make fat soluble nutrients embedded. Therefore in the process of preparing the stable, fat-soluble nutrients microcapsule, an emulsion of mixing aqueous phase with oil phase is homogenized by high pressure homogenization in order to sufficiently make droplets smaller and ensure droplets of the oil phase in a dispersed state is effectively embedded by capsule shell materials, so as to improve the stability thereof.

However, in the process of high pressure homogenization, it would inevitably make an emulsion temperature and pressure obviously increase if it need to provide more energy. Increasing an emulsion temperature is very unfavorable for the nutrients containing double bonds because the double bonds mainly make nutrients unstable, and consequently become an oxidizing agent in human body. It needs timely elimination of free radicals in the human body. Therefore, increase of temperature in the preparation process of microcapsules inevitably produces a negative effect on the stability of the double bonds. For example, DHA and EPA of fish oil ω-3 polyunsaturated fatty acids are highly sensitive to temperature. Higher temperatures not only degrades EPA and DHA and reduces their biological activity, but also makes final products produce unpleasant odors, thereby affecting its application.

It is necessary to obtain a smaller particle diameter droplet by applying high pressure homogenization. The smaller the droplet particle diameter, the higher the pressure required. However, high pressure would greatly increase the emulsion temperature, and consequently would seriously damage the effective components of the emulsion. Therefore the pressure of the homogenization and particle size of the droplet certainly are contradictory. The contradiction would be solved if the droplet of the emulsion can be homogenized to a smaller particle diameter under a lower pressure.

The present inventors found that the viscosity of the pre-homogenization emulsion largely influences the homogeneous pressure for the droplet particle diameter with the same requirement. The lower the viscosity, the favorabler the homogenization. That is to say, the lower the emulsion viscosity, the lower the homogeneous pressure, in order to achieve the same particle diameter of the droplet. It inevitably makes temperature not obvious to increase when homogeneous, and less damage to the nutrients. Therefore, the emulsion temperature increases no more than 10° C. relative to the pre-homogenization temperature in the process of high pressure homogenization. The homogenization pressure is in a range of 10 MPa to 40 MPa.

In the present invention, a part but not all of the capsule shell material is dissolved in a certain amount of water to obtain an aqueous phase. It can assure that the viscosity of the emulsion is lower when the oil phase is embedded, so that the pressure would be much lower in subsequent homogenization, thereby effectively reducing the level of temperature increasing in the process of high pressure homogenization, and thus reduce the damage to the nutrients. According to the differences of the embedding capacity, the amount of pre-dissolved capsule shell material is in a range of 15 wt %~85 wt % of the total amount of capsule shell material.

The remaining capsule shell material is directly added to the homogeneous emulsion without a dissolving process of adding water after homogenizing. The capsule shell material is dissolved after shearing and mixing, and then embedded in the nanoscale nutrient droplets to form twice-embedded emulsion. It would be more beneficial to increase the stability of the nutrient microcapsule. Another advantage of directly adding the capsule shell material in a later period is to effectively control the solid content and viscosity of the emulsion before spray granulation, and without any additional concentrated dehydration process.

The obtained emulsion may be dried by conventional prilling process such as spray drying, spray starch bed fluidized drying, spray multi-stage starch bed fluidized drying, and then eventually obtain the microcapsule powders or microparticles product.

The present invention creatively provides a method of firstly dissolving a part of a capsule shell material into water to obtain an aqueous phase, and mixing with an oil phase and shearing and emulsifying to form an emulsion, and then homogenizing the emulsion at low pressure, adding a remaining portion of the capsule shell material into the emulsion; directly spraying granulating the emulsion after it is completely dissolved to obtain a microcapsule product. The microcapsule product is quite stable without an objectionable odor after storage for extended periods of time. More importantly, the microcapsule powders or microparticles obtained by the method of the present invention have better stability. The microcapsule powders or microparticles also have better stability without bad odors, even after tabletting with high pressure. Therefore the microcapsule powders or microparticles are suitable for the field of foods and dietary supplement.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

Mix 48 g of fish oil ☐ω-3 fatty acid ethyl ester (EPA 33.5%, DHA 23.1%, total content of ω-3 PUFA is 59.8%)

with 2 g of mixed tocopherols to form a solution, and stir the solution at 30° C. until homogeneous to obtain an oil phase.

Add 10 g of modified starch to 80 ml water, and raise the temperature to 40° C., and fully stir and dissolve to obtain an aqueous phase.

Add the aqueous phase to a shear tank, and shear and stir, at the same time slowly add the oil phase to the aqueous phase, to make the oil phase and the aqueous phase fully shear, mix and emulsify, to obtain an emulsion. The emulsion temperature should be 52° C. and the viscosity of the emulsion should be 8.5 cPa after completion of the emulsification. The emulsion is then homogenized by a high Pressure Homogenizer (made by Changzhou homogeneous Machinery Co., Ltd. Type: GJB1000-80, homogenization pressure: 30 MPa). After homogenization, the temperature of the emulsion is up to 59° C. (the increased temperature is 7° C., the average particle diameter of the emulsion droplet measured by a laser particle size distribution instrument is 580 nm.

Add 20 g modified starch to the homogenized emulsion under shearing and stirring for 10 min, to form a twice-embedded emulsion outside the emulsion droplets after the modified starch is completely dissolved, to finally obtain 160 g of the emulsion and the solid content is 50 wt %; and then obtain fish oil ω-3 fatty acid ethyl ester microcapsule microparticles by a common technique of spray starch bed fluidized drying (20 g modified starch is absorbed), wherein the polyunsaturated fatty acids content is 26.5%.

The fish oil ω-3 fatty acid ethyl ester microcapsule microparticles have good dispersibility in water, with the average particle diameter being 633 nm of the emulsion droplet. The microparticles after tabletting the microparticles under a pressure 250 MPa still have good stability. The microcapsule microparticles are sealed in an aluminum foil bag. The stability data of the sealed microcapsule microparticles at 40° C. is provided in Table 1.

The obtained microcapsule microparticles are placed in a jar, and then odors are measured by using an electronic nose, a quantitative value of the electronic nose is 23.5. Afterwards the jar is kept in a water bath at 60° C. for 10 min, and then odors are measured by using an electronic nose again, and a quantitative value of the electronic nose is 27.6. The odor change of the microcapsule microparticles is found to be less.

Comparative Example 2

Mix 48 g fish oil ☐ω-3 fatty acid ethyl ester (EPA 33.5%, DHA 23.1%, total content of ω-3 PUFA is 59.8%) with 2 g mixed tocopherols to form a solution, and stir the solution at 30° C. until homogeneous to obtain an oil phase.

Add 30 g modified starch to 100 ml water, raise the temperature to 40° C., and stir and dissolve to obtain an aqueous phase.

Add the aqueous phase to a shear tank, and shear and stir, at the same time slowly add the oil phase to the aqueous phase, to make the oil phase and the aqueous phase fully shear, mix and emulsify, to obtain an emulsion. The emulsion temperature was at 45° C. and the viscosity of the emulsion was 90 cPa after completion of the emulsification. The emulsion is then homogenized by a high Pressure Homogenizer with a homogenization pressure of 50 MPa. After homogenization, the temperature of the emulsion was 72° C. (the increase in temperature was 27° C.) the average particle diameter of the emulsion droplet measured by a laser particle size distribution instrument was 1380 nm.

Finally, obtain 180 g of the emulsion and the solid content is 44.5 wt %; and then obtain fish oil ω-3 fatty acid ethyl ester microcapsule microparticles by a common technique of spray starch bed fluidized drying (25 g modified starch is absorbed), wherein the polyunsaturated fatty acids content is 24.7%.

The fish oil ω-3 fatty acid ethyl ester microcapsule microparticles have good dispersibility in water, with an average particle diameter of 1420 nm of the emulsion droplet. The microparticles after tableting the microparticles under a pressure 250 MPa have poor stability. The microcapsule microparticles are sealed in an aluminum foil bag. The stability data of the sealed microcapsule microparticles at 40° C. is listed in Table 1.

The obtained microcapsule microparticles are placed in a jar, and then the odor level is measured by using an electronic nose, with a quantitative value of the electronic nose being 89.3. Afterwards the jar is kept in a water bath at 60° C. for 10 minutes, and then odors were again measured by using the electronic nose, and a quantitative value of the electronic nose was 223.8. The odors of the microcapsule microparticles were found to be very strong and were especially so after heating.

It may be seen by comparison that the viscosity of the emulsion of Example 1 is still lower in the case of adding less water due to add a small amount of capsule shell materials before homogenization. After the emulsion is homogenized at a relatively low pressure, the average particle diameter of the emulsion droplet is only 500 nm. Moreover, the emulsion temperature is increased less (only increased by 7° C.). Therefore it would have less damage to the stablity of the fish oil ω-3 PUFA, no new low molecular material is produced. Therefore the final products are kept without fishy odors being produced during storage. The average particle diameter of the emulsion droplet in the final microcapsule microparticles is 630 nm. The smaller particle diameter emulsion droplet are beneficial to the stability of the final products. Further, subsequently adding the capsule shell materials can form a twice-embedded emulsion, so as to further be beneficial to the stablity of the microcapsule microparticles. After high pressure tableting, the microcapsule microparticles were stored for 3 months and the retention rate was still found to be more than 87%.

On the contrary, in Comparative Example 2, adding at once the capsule shell materials before high pressure homogenization makes the viscosity of the emulsion higher and increases the homogenization pressure. However, the average particle diameter of the emulsion droplet is whereas micron-scale. And the homogenization time is extended and the homogenization temperature is obviously increased during homogenization up to 27° C. It makes parts of the polyunsaturated fatty acids degrade and produce strong fishy odors. Moreover, the stability of the final product and tabletted product are obviously less than that of Example 1.

TABLE 1

Stability Comparison of fish oil ω-3 fatty acid ethyl ester microcapsule microparticles
and tabletted product obtained by different processes (sealed in aluminium foil bag at 40° C.)

| Time (month) | Example 1 microparticles content | Example 1 microparticles Retention rate | Example 1 tabletted content | Example 1 tabletted Retention rate | Example 2 microparticles content | Example 2 microparticles Retention rate | Example 2 tabletted content | Example 2 tabletted Retention rate |
|---|---|---|---|---|---|---|---|---|
| 0 | 26.5% | 100% | 26.5% | 100% | 24.7% | 100% | 24.7% | 100% |
| 1 | 25.8% | 97.4% | 24.4% | 92.1% | 22.4% | 90.5% | 21.0% | 85.0% |
| 2 | 25.2% | 95.2% | 23.4% | 88.4% | 21.7% | 87.8% | 19.6% | 79.8% |
| 3 | 24.9% | 94.0% | 23.2% | 87.7% | 21.1% | 85.6% | 18.7% | 75.9% |

Example 3

Mix 20 g lutein crystals (total content of carotenoids is 87.5%, wherein the ratio of zeaxanthin is 13.2%) with 4.5 g synthetic tocopherols, and heat to 180° C. until melting to form an oil phase.

Add 35 g gelatin to 210 ml water, and fully dissolve at a temperature to 40° C. to obtain an aqueous phase, and add ascorbic acid sodium to the aqueous phase to obtain an aqueous phase.

Slowly add the oil phase to the aqueous phase under shearing, and fully shear, mix and emulsify the oil phase and the aqueous phase for 10 minutes to obtain an emulsion. The viscosity of the emulsion is 120 cPa. The emulsion is then homogenized by a Homogenizer, the homogenization pressure is 25 MPa. After homogenization, the temperature of the emulsion is 72° C. (the increased temperature is 5° C.) the average particle diameter of the emulsion droplet measured by a laser particle size distribution instrument is 158 nm.

35 g gelatin and 64 g sucrose are added to the homogenized emulsion in the case of shearing, and continue to shear and mix for 10 minutes to obtain lutein microcapsule dry powders containing zeaxanthin by spray drying.

Dissolve the lutein microcapsule powders in water to obtain the emulsion with 164 nm particle diameter. The lutein microcapsule powders have good stability. The retention rate of the tabletted lutein microcapsule powders after tabletting is still more than 85% in the case of open storage at 40° C. for 3 months.

Examples 4-9

TABLE 2

The implement objects and related parameters of Examples 4-9

| | Example 3 | Example 4 | Example 5 | Example6 | Example 7 | Example 8 | Example 9 |
|---|---|---|---|---|---|---|---|
| Type and Quantity of active ingredients | 12 g conjugated linoleic acid, 3 g linoleic acid | 45 g curcumin | 10 g astaxanthin, 10 g lycopene, 5 g beta-carotenes | 15 g coenzymes Q10, 25 g reduced Coenzyme Q10 | 15 g arachidonic acid (AA), 5 g linolenic | 21 g algae DHA | 15 g vitamin A, 30 g vitamin E, 2 g vitamin D3, 30 g natural vitamin E |
| pre-addition amount of capsule shell material | 15 g gum Arabic | 85 g gelatin | 9.0 g modified starch | 30 g sodium caseinate | 10 g modified starch | 50 g modified starch | 10 g gelatin |
| Quantity of water added in aqueous phase | 50 ml | 150 ml | 150 ml | 90 ml | 60 ml | 180 ml | 70 ml |
| Antioxidant | 4.0 g lecithin | 6.0 g vitamin C | 3.0 g ascorbyl palmitat | 4.0 g sodium ascorbate | 2.0 g rosemary | 9.0 g ascorbyl palmitat | 3.5 g mixed tocopherols |
| Viscosity of emulsion before homogenization (cPa) | 4.5 | 7.9 | 5.4 | 9.4 | 2.1 | 3.2 | 5.6 |
| Homogenization pressure | 20 MPa | 30 MPa | 25 MPa | 25 MPa | 10 MPa | 20 MPa | 40 MPa |
| Increased temperature during the homogenization | 6° C. | 10° C. | 6° C. | 9° C. | 4° C. | 5° C. | 7° C. |
| additional amount of capsule shell material | 26 g | 15 g | 51.0 g | 30.0 g | 35 g | 150 g | 10 g |
| average particle diameter of emulsion droplet | 345 nm | 790 nm | 370 nm | 685 nm | 420 nm | 520 nm | 730 nm |
| Drying mode | Fluid bed spray drying | Fluid bed spray drying | Fluid bed spray drying | Spray drying | Freeze drying | Spray drying | Fluid bed spray drying |

TABLE 2-continued

The implement objects and related parameters of Examples 4-9

|  | Example 3 | Example 4 | Example 5 | Example6 | Example 7 | Example 8 | Example 9 |
|---|---|---|---|---|---|---|---|
| retention rate of microcapsule product after storing for 3 month | 91.2% | 94.6% | 96.2% | 93.2% | 93.7% | 92.6% | 90.0% |
| retention rate of tabletted microcapsule product after storing for 3 month | 85.0% | 92.5% | 93.5% | 87.9% | 84.9% | 89.2% | 88.5% |

The experiment of the present invention shows that the microcapsule powders or microparticles prepared by the method of the present invention have good stability.

The present invention as illustrated by the above examples, however, should understand that the present invention is not limited to the special instance and implementation scheme described herein. These special examples and implementation plans are aimed at helping the person skilled in the art to practice the present invention. The person skilled in the art is easily able from the spirit and scope of the present invention to further improve and perfect, so the present invention only is restricted by the content and scope of the claims of the present invention, and its intention to cover all in the alternative solutions and equivalent solutions which are included in the appended claims without limiting the scope of the invention.

The invention claimed is:

1. A method of preparing highly stable microcapsule powders or microparticles containing a fat-soluble nutrient having multiple double bonds, comprising the following steps:
    a) dissolving a fat-soluble nutrient having multiple unsaturated double bonds to prepare an oil phase;
    b) dissolving a part of a capsule shell material in water to prepare an aqueous phase;
    c) shearing the aqueous phase and the oil phase, and mixing and emulsifying the same to obtain an emulsion;
    d) homogenizing the emulsion by a standard high-pressure homogenizer to make the emulsion obtain droplets in the emulsion with an average particle diameter at a nanometer level, thereby producing a nanometer scale emulsion;
    e) directly adding a remaining part of the capsule shell material into the homogenized nanometer scale emulsion, and shearing, mixing and dissolving the same to obtain a twice-embedded emulsion; and
    f) performing spray granulation on the twice-embedded emulsion, and drying resultant granules to obtain highly stable microcapsule powders or microparticles, wherein the capsule shell material of step b) and the remaining part of the capsule shell material of step e) are the same material, and is selected from the group consisting of modified starch, gelatin, gum Arabic, and sodium caseinate.

2. The method according to claim 1, wherein the fat-soluble nutrient having multiple unsaturated double bonds is selected from the group consisting of VA, VE, natural VE, VD3, coenzymes 10, curcumin, carotenoid and polyunsaturated fatty acid.

3. The method according to claim 2, wherein the carotenoid is selected from the group consisting of beta-carotene, lutein, astaxanthin, lycopene, and zeaxanthin; the polyunsaturated fatty acid is derived from a source selected from the group consisting of animal extract oil, fermented source and a synthetic source; the polyunsaturated fatty acid is selected from the group consisting of conjugated linoleic acid, arachidonic acid, linoleic acid, linolenic acid, eicosapentaenoic acid (EPA), docosahexaenoic acid (DHA), and a mixture thereof.

4. The method according to claim 1, wherein the aqueous phase or the oil phase further comprises an antioxidant.

5. The method according to claim 4, wherein the antioxidant is selected from the group consisting of vitamin C, ascorbyl palmitate, mixed tocopherols, synthetic tocopherols, sodium ascorbate, and rosemary.

6. The method according to claim 1, wherein in step b) an amount of the capsule shell material in the aqueous phase is in a range of 15-85 wt. % of the total amount of the capsule shell material, when preparing the aqueous phase.

7. The method according to claim 1, wherein, in the process of high pressure homogenization of step d), a temperature of the emulsion after homogenizing is increased no more than 10° C. relative to a temperature of pre-homogenizing.

8. The method according to claim 1, wherein in the process of high pressure homogenization of step d) a homogenization pressure is in a range of 10 MPa to 40 MPa.

* * * * *